United States Patent [19]

Chari et al.

[11] Patent Number: 5,627,017

[45] Date of Patent: May 6, 1997

[54] LOW MELTING POINT IONIZABLE EPOXY SCAVENGERS FOR RESIDUAL MAGENTA COUPLERS

[75] Inventors: Krishnan Chari; Paul P. Spara, both of Fairport; Sundaram Krishnamurthy, Penfield, all of N.Y.

[73] Assignee: Eastman Kodak Company, Rochester, N.Y.

[21] Appl. No.: 427,764

[22] Filed: Apr. 25, 1995

[51] Int. Cl.$^6$ .................................... G03C 7/388
[52] U.S. Cl. .................. 430/546; 430/545; 430/551; 430/554; 430/555; 430/558; 430/638; 430/935
[58] Field of Search ................... 430/545, 546, 430/551, 554, 555, 558, 638, 935

[56] References Cited

U.S. PATENT DOCUMENTS

| | | | |
|---|---|---|---|
| 3,936,303 | 2/1976 | Shiba et al. | 430/546 |
| 4,239,851 | 12/1980 | Aoki et al. | 430/377 |
| 4,540,657 | 9/1985 | Krishnamurthy | 430/546 |
| 4,745,052 | 5/1988 | Renner | 430/555 |
| 4,900,655 | 2/1990 | Nakazyo et al. | 430/546 |
| 5,001,045 | 3/1991 | Furutachi et al. | 430/545 |
| 5,037,730 | 8/1991 | Aoki et al. | 430/551 |
| 5,047,315 | 9/1991 | Morigaki et al. | 430/544 |
| 5,183,731 | 2/1993 | Takahashi et al. | 430/551 |
| 5,200,307 | 4/1993 | Takahashi | 430/507 |
| 5,543,276 | 5/1990 | Chari et al. | 430/505 |

FOREIGN PATENT DOCUMENTS

| | | |
|---|---|---|
| 435179 | 7/1991 | European Pat. Off. . |
| 0471347 | 2/1992 | European Pat. Off. . |
| 0472153 | 2/1992 | European Pat. Off. . |
| 472153 | 2/1992 | European Pat. Off. . |
| 471347 | 2/1992 | European Pat. Off. . |
| 476604 | 3/1992 | European Pat. Off. . |
| 2432041 | 1/1975 | Germany . |
| 62-75448 | 4/1987 | Japan . |
| 62-131259 | 6/1987 | Japan . |
| 62-166331 | 7/1987 | Japan . |
| 62-201441 | 9/1987 | Japan . |

OTHER PUBLICATIONS

Derwent Abstract for Japanese Application No. 62/80,641.
Derwent Abstract for Japanese Application No. 62/129,853.
Derwent Abstract for Japanese Application No. 63/250,652.

*Primary Examiner*—Lee C. Wright
*Attorney, Agent, or Firm*—Andrew J. Anderson

[57] ABSTRACT

Low melting point epoxy scavenger compounds are disclosed which contain a pH dependent ionizable group to facilitate migration of the scavenger from an adjacent scavenger layer (that does not contain any coupler) to an imaging layer (containing coupler and emulsion) of a photographic element at the pH of development. One aspect of the invention comprises a process of forming an aqueous dispersion of an epoxy compound of the structural formula SI:

$$L_2-(L_3)_p-\underset{\underset{X}{\underset{|}{(L_1)_m}}}{\overset{|}{CH}}-\overset{O}{\overset{/\backslash}{CH-CHR}} \quad SI$$

wherein: R is H, an alkyl group, or an aryl group; $L_1$ is an alkyl group or an aryl group; $L_2$ is —O—, —CO—, —S—, —SO$_2$—, —PO$_2$—, —CO$_2$—, —NHCO— or —NHSO$_2$—, wherein $L_2$ may be orientated in either direction; $L_3$ is an alkyl group; m is 0 or 1; p is 0 or 1; and X is $$-\underset{\underset{OR'}{|}}{\overset{\overset{O}{\|}}{P}}-OH, \quad or \quad -\underset{\underset{OR'}{|}}{B}-OH$$

wherein R' is H or an alkyl or aryl group, with the proviso that where $L_2$ comprises an ionizable group, X may also be an alkyl group or an aryl group; wherein the compound has a melting point of less than about 50° C. and the process comprises adding the compound in a liquid state to an aqueous solution, and directly dispersing the compound in the aqueous solution. Thermal and photochemical yellowing of a color photographic element, such as a color print, is inhibited by incorporating such compounds into the photographic element.

8 Claims, No Drawings

LOW MELTING POINT IONIZABLE EPOXY SCAVENGERS FOR RESIDUAL MAGENTA COUPLERS

FIELD OF THE INVENTION

This invention relates to a method of forming dispersions of novel epoxy compounds useful in multilayer silver halide color photographic elements. This invention further relates to a color photographic element comprising such dispersions having improved resistance to thermal and photochemical yellowing.

BACKGROUND OF THE INVENTION

It is well known that thermal and photochemical yellowing are major concerns in magenta image stability of color prints. Over the years improvement in magenta image stability has been achieved by introducing more efficient image stabilizers. However, there still exists a need to further improve the resistance to yellowing in color paper.

It has been known for some time that compounds having the generic structure S are able to undergo reaction with residual magenta coupler and thereby effectively prevent both thermal and photochemical yellowing since the products of the reaction are not yellow and are not prone to yellowing. However, a major problem in the utilization of these compounds is the loss of coupler during storage of the photographic element prior to exposure and processing resulting in a reduction in color density in the print. See for example, U.S. Pat. No. 4,540,657 to Krishnamurthy and Japanese Patent Publication No. 62-131259 to Fuji Photo Film Co., Ltd. The generic structure of Compound S is represented below:

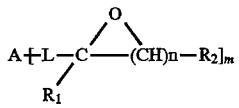

S wherein: A is a polyvalent atom, an acidic oxide group, a carboxylic group, a heterocyclic moiety, a carbocyclic group, or an alkane or substituted alkane group; each L is at least one divalent linking group; $R_1$ and $R_2$ are H, alkyl, cycloalkyl, aryl, heterocyclic, ester; n is a positive integer with a range of 1–6; m is a positive integer of at least one; with the proviso that at least one of A, L, $R_1$ or $R_2$ contains at least one ester or amide group derived from an acidic oxide of carbon, phosphorous, sulfur, boron or silicon.

In copending, commonly assigned application U.S. Ser. No. 08/000,431, filed Jan. 4, 1993, we showed that the compound S-1 (having the structural formula set forth below) could be incorporated in a silver halide color photographic element containing a ballasted magenta coupler such that there is negligible loss of coupler prior to processing. This was achieved by coating the epoxy compound in separate layers that were adjacent to the imaging layer containing the magenta coupler and the green sensitized emulsion. Furthermore, it has also been demonstrated that mixing of S-1 with residual magenta coupler after processing may be achieved by using a pH dependent solubilizing agent, e.g., a fatty acid, such as myrisitic acid, in the coating and processing the coating using developer which preferably contains benzyl alcohol. However, the use of benzyl alcohol in the developer raises environmental concerns.

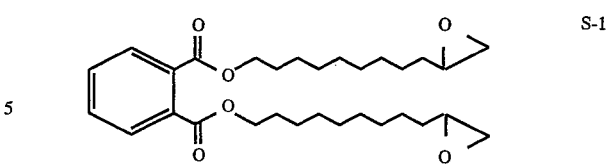

S-1

In an effort to eliminate the use of compounds such as benzyl alcohol to achieve post process mixing of the epoxy scavenger with the residual magenta coupler, copending, commonly assigned U.S. Ser. No. 08/255,512, filed Jun. 8, 1994, discloses novel terminal epoxy compounds containing a pH-dependent solubilizing moiety in the molecule. Dispersions of these compounds are coated in layers adjacent to the magenta imaging layer, and the compounds diffuse into the magenta layer upon processing where they react with residual magenta coupler yielding products that are not yellow or prone to yellowing. The approach is effective in reducing thermal and photochemical yellowing in processed prints without the use of benzyl alcohol.

Hydrophobic photographic additives are conveniently incorporated in a hydrophilic colloid layer of a photographic element by dissolving the hydrophobic additive in an organic solvent and then dispersing the organic solution in an aqueous solution to form a homogenized dispersion. The epoxy compounds exemplified in U.S. Ser. No. 08/255,512, however, are generally characterized by a relatively high melting point (greater than 50° C.) and low hydrophobicity (the logarithm of the octanol/water partition coefficient (logP) for these compounds is less than 8.0). The low hydrophobicity is essential to achieve efficient post-process migration of these compounds from the adjacent non-imaging layers into the magenta imaging layer. The combination of low hydrophobicity and high melting point makes it difficult to prepare stable dispersions of these compounds by homogenization in an aqueous solution even if relatively large amounts of water-immiscible organic solvent is used to dissolve the compounds. The exemplified compounds are accordingly dispersed in the examples of U.S. Ser. No. 08/255,512 by a solid particle dispersion process. In this method size reduction of the epoxy compound is achieved by attrition with media such as zirconia beads instead of by shearing action on a liquid solution. The solid particle dispersion process is relatively inefficient compared to homogenization and often requires several days of grinding in order to achieve the desired level of size reduction.

Problem to be Solved by the Invention

It would be most desirable to have ionizable terminal epoxy compounds of low hydrophobicity that could be incorporated in the photographic element as homogenized dispersions. It is towards this end that the present invention is directed.

SUMMARY OF THE INVENTION

It is the object of this invention to provide a silver halide based color photographic element having vastly superior image stability over prior art processes.

It is a further object of this invention to provide a silver halide based color photographic element containing novel terminal epoxy compounds having low hydrophobicity (logP less than 8.0) and a pH-dependent ionizable moiety.

It is a still further object of this invention to provide a silver halide based color photographic element containing a new class of said novel terminal epoxy compounds that are liquid at room temperature or which have a sufficiently low melting point to enable stable homogenized dispersions to be formed thereof. These new compounds are characterized by a melting point less than about 50° C., preferably less than 25° C., more preferably less than 20° C.

It is a still further object of this invention to provide a silver halide based color photographic element containing homogenized dispersions of said novel terminal epoxy compounds.

These objects are realized by using novel low-melting point epoxy scavenger compounds that contain a pH dependent ionizable group to facilitate migration of the scavenger from the adjacent scavenger layer (that does not contain any coupler) to the imaging layer (containing coupler and emulsion) at the pH of development.

One aspect of this invention comprises a process of forming an aqueous dispersion of an epoxy compound of the structural formula SI:

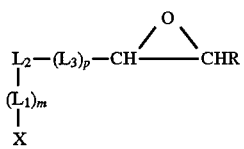

wherein: R is H, an alkyl group, or an aryl group; $L_1$ is an alkyl group or an aryl group; $L_2$ is —O—, —CO—, —S—, —SO$_2$—, —PO$_2$—, —CO$_2$—, —NHCO— or —NHSO$_2$—, wherein $L_2$ may be orientated in either direction; $L_3$ is an alkyl group; m is 0 or 1; p is 0 or 1; and X is —NHSO$_2$R', —SO$_2$NHR',

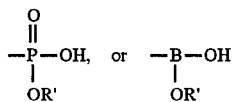

wherein R' is H or an alkyl or aryl group, with the proviso that where $L_2$ comprises an ionizable group, X may also be an alkyl group or an aryl group; wherein the compound has a melting point of less than about 50° C. and the process comprises adding the compound in a liquid state to an aqueous solution, and directly dispersing the compound in the aqueous solution.

A further aspect of this invention comprises a method of preparing a photographic element comprising coating on a support (a) a photosensitive first layer comprising (i) a silver halide emulsion and (ii) a magenta coupler dispersed therein; and (b) a second layer comprising an epoxy compound dispersion prepared as described above.

Yet another aspect of this invention comprises a photographic element comprising a support bearing (a) a photosensitive first layer comprising (i) a silver halide emulsion and (ii) a magenta coupler dispersed therein; and (b) a second layer comprising an epoxy compound dispersion prepared as described above.

Advantageous Effect of the Invention

The novel ionizable epoxy compounds can be added to a photographic element to inhibit the thermal and photochemical yellowing of color photographic elements in the form of a stable homogenized photographic dispersion.

Detailed Description of the Invention

The alkyl and aryl groups in Formula SI can be unsubstituted or further substituted with photographically acceptable substituents. Typical examples of photographic substituents include alkyl, aryl, anilino, carbonamido, sulfonamido, alkylthio, arylthio, alkenyl, cycloalkyl, and further to these exemplified are halogen, cycloalkenyl, alkinyl, heterocyclyl, sulfonyl, sulfinyl, phosphonyl, acyl, carbamoyl, sulfamoyl, cyano, alkoxy, aryloxy, heterocyclyloxy, siloxy, acyloxy, carbamoyloxy, amino, alkylamino, imido, ureido, sulfamoylamino, alkoxycarbonylamino, aryloxycarbonylamino, alkoxycarbonyl, aryloxycarbonyl, heterocyclylthio, spiro compound residues and bridged hydrocarbon compound residues. Usually the substituent will have less than 30 carbon atoms and typically less than 20 carbon atoms. It is understood throughout this specification that any reference to a substituent by the identification of a group containing a substitutable hydrogen (e.g. alkyl, amine, aryl, alkoxy, heterocyclic, etc.), unless otherwise specifically stated, shall encompass not only the substituent's unsubstituted form, but also its form substituted with any other photographically useful substituents. Preferred substituents on the alkyl and aryl groups of Formula SI are hydrocarbyl groups, one or more hetero atoms, such as chlorine and the like or one or more hetero groups containing for example, N, P, S, etc. R in Formula SI is preferably H or alkyl, such as methyl, ethyl, etc Preferred compounds for use in the invention include those of Formula SI wherein m and p are each 1, $L_1$ is phenyl, $L_2$ is —O—, —CO—, —SO2—, —PO2—, or —CO2—, $L_3$ is a linear or branched alkyl group, X is —NHSO$_2$R', —SO$_2$NHR',

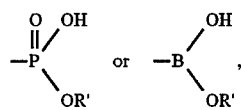

and R' is a phenyl group. Most preferred are compounds of the formula:

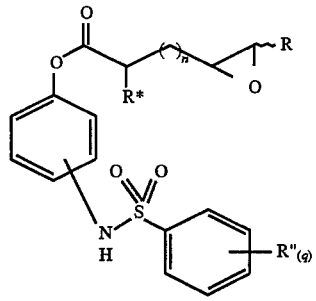

wherein: R* is H or an alkyl or aryl group; n is from 1 to about 20; q is 1, 2, or 3; and each R" is H, an alkoxide group, a phosphate group, a sulfate group, a sulfonamide group, a sulfone group, a halogen atom, or an alkyl group; with the proviso the appended sulfonamido group is in a meta or para position with respect to the —CO$_2$— linking group, and with the further proviso when the appended sulfonamido group is in the para position each R" is H, or at least one appended R" group which is not H is in the meta or ortho position with respect to the —NHSO$_2$— linking group, or R* is not H. Substitution in the ortho or meta position on the phenyl rings has been found to generally result in lower melting points than comparable para-substituted compounds, and the addition of a chiral center (a carbon atom having four different substituents, such as where R* is other than H) also tends to lower melting point in comparison to analogous compounds. Additionally, compounds wherein each R" is H (i.e., wherein the phenyl substituent is unsubstituted) have also been found to result in generally lower melting points than compounds wherein the phenyl ring is substituted. Accordingly, compounds satisfying the above preferred provisos have been found to generally have lower melting points than compounds which do not meet such provisos,
The following are illustrative examples of the structures of low melting or liquid residual magenta coupler scavengers:
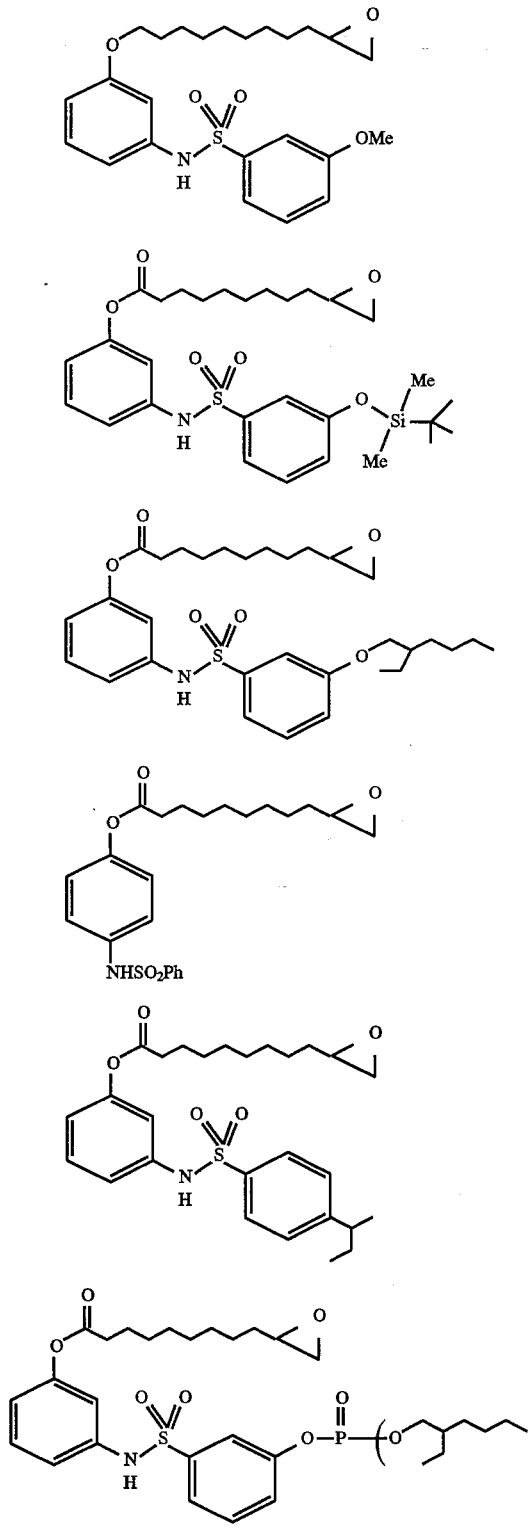
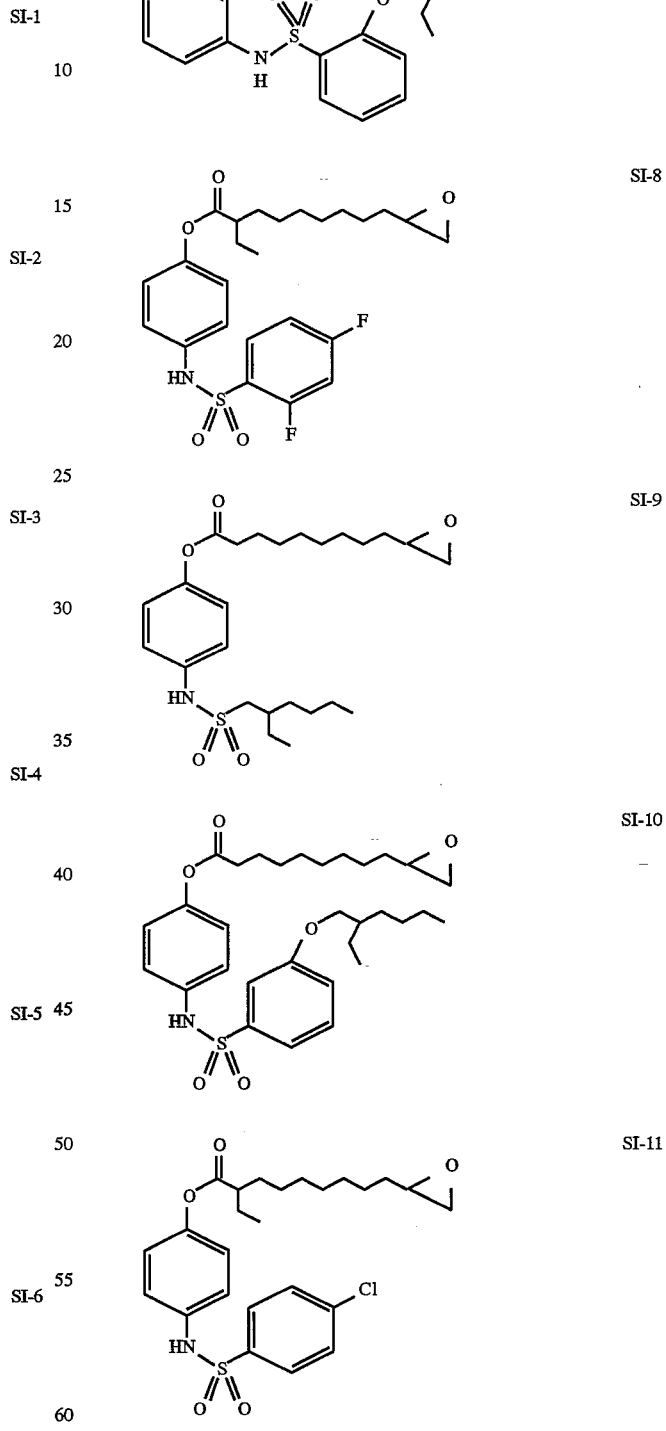

SI-12

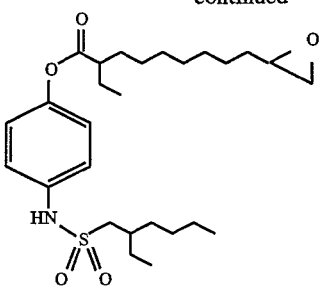

SI-13

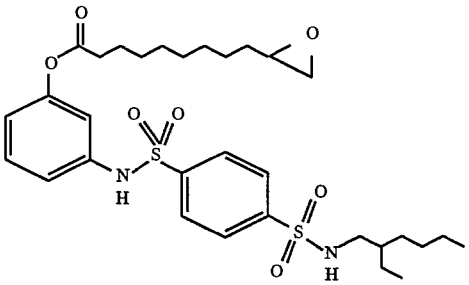

SI-14

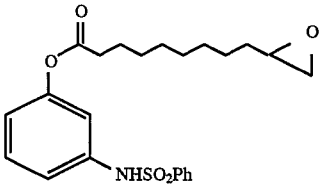

SI-15

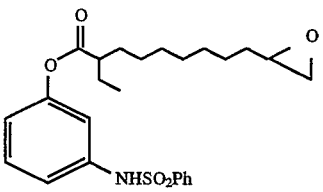

SI-16

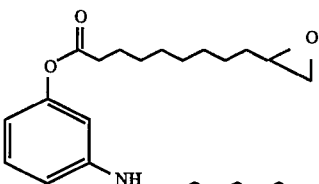

SI-17

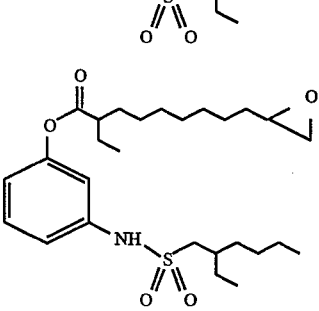

The scavengers of the present invention may be synthesized by a process which comprises of reacting an amino phenol (meta or para substituted) of the formula (1) with a substituted or unsubstituted sulfonyl chloride of the formula (2) in the presence of a suitable solvent and base to obtain intermediate sulfonamido phenol (A). Acetonitrile and pyridine are one such suitable solvent and base for this reaction. In accordance with the invention, R' may be an alkyl or aryl group, the nature of the substitutient being one that confers the property of relative low melting point or liquid state for the resulting epoxy compound.

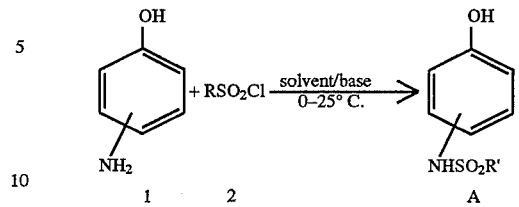

Intermediate A can then be allowed to react with an acid chloride (3) with a desired level of lipophilicity and containing a terminal olefin in a solvent such as refluxing acetonitrile in the absence of base to give the intermediate ester sulfonamide (B). In accordance with the invention, R*=H, or an alkyl or aryl group.

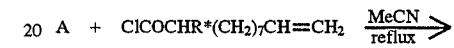

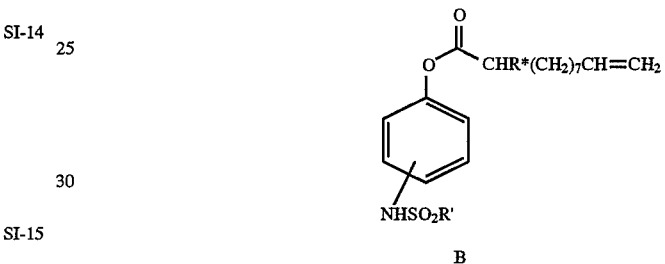

Intermediate B can then be epoxidized under typical conditions (m-CPBA (4)/$CH_2Cl_2$) to give the desired ionizable residual magenta coupler scavenger (C).

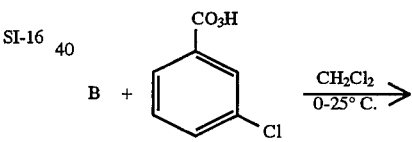

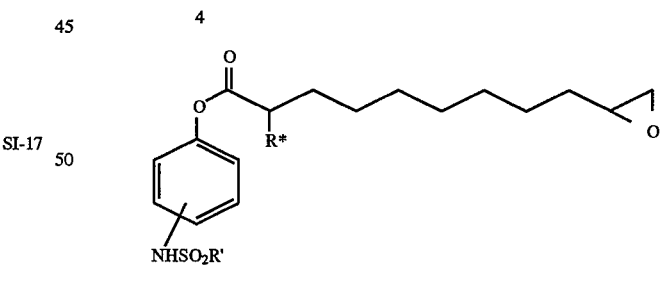

The process of the invention comprises adding an organic compound of Formula SI in a liquid state to an aqueous solution, and directly dispersing the compound in the aqueous solution. The dispersions may be prepared by means known in the art, such as by mixing under conditions of high shear or turbulence. While the low melting compounds of the invention are preferably liquid at room temperature, or may be liquefied at moderately raised temperatures, the liquid state organic, or oil phase, components of such dispersions may additionally include high-boiling organic solvents, known as oil formers, coupler solvents, or permanent solvents. High boiling solvents have a boiling point sufficiently high, generally above 150° C. at atmospheric pressure, such that they are not evaporated under normal dispersion making and photographic layer coating procedures. It is an advantage of the invention that the low melting compounds of the invention form dispersions which are more stable than comparative high-melting compound dispersions formed with organic solvents. Non-limitive examples of high boiling organic solvents that may be used include the following.

| | |
|---|---|
| S1 | Dibutyl phthalate |
| S2 | Tritolyl phosphate |
| S3 | N,N-Diethyldodecanamide |
| S4 | Tris(2-ethylhexyl)phosphate |
| S5 | Octyl oleate monoepoxide |
| S6 | 2,5-Di-t-pentylphenol |
| S7 | Acetyl tributyl citrate |
| S8 | 1,4-Cyclohexylenedimethylene bis(2-ethylhexanoate) |
| S9 | Bis(2-ethylhexyl) phthalate |
| S10 | 2-phenylethyl benzoate |
| S11 | Dibutyl sebacate |
| S12 | N,N-Dibutyldodecanamide |
| S13 | Oleyl alcohol |
| S14 | 2-(2-Butoxyethoxy)ethyl acetate |

Auxiliary solvents may also be included in dispersion making processes. Many useful auxiliary solvents are water immiscible, volatile solvents, and solvents with limited water solubility which are not completely water miscible. Examples of these include the following.

| | |
|---|---|
| A1 | Ethyl acetate |
| A2 | Cyclohexanone |
| A3 | 4-Methyl-2-pentanol |
| A4 | Triethyl phosphate |
| A5 | Methylene chloride |
| A6 | Tetrahydrofuran |

The aqueous phase of the dispersions used in the invention may comprise a hydrophilic colloid, preferably gelatin. This may be gelatin or a modified gelatin such as acetylated gelatin, phthalated gelatin, oxidized gelatin, etc. Gelatin may be base-processed, such as lime-processed gelatin, or may be acid-processed, such as acid processed ossein gelatin. The hydrophilic colloid may be another water-soluble polymer or copolymer including, but not limited to poly(vinyl alcohol), partially hydrolyzed poly(vinylacetate/ vinylalcohol), hydroxyethyl cellulose, poly(acrylic acid), poly(1-vinylpyrrolidone), poly(sodium styrene sulfonate), poly(2-acrylamido-2-methane sulfonic acid), polyacrylamide. Copolymers of these polymers with hydrophobic monomers may also be used.

The dispersions and coated layers of the elements of the invention may include surfactants. Surfactants may be cationic, anionic, zwitterionic or non-ionic. Ratios of surfactant to liquid organic solution typically are in the range of 0.5 to 25 wt. % for forming small particle photographic dispersions, which ratios are also useful for forming the invention dispersions. Useful surfactants include, but are not limited the following.

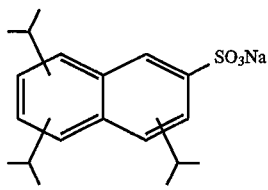

F1

$CF_3(CF_2)_7SO_3Na$     F2
$CH_3(CH_2)_nSO_3Na$, n = 12–14     F3

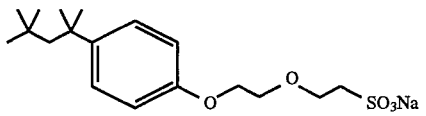

F4

$CH_3(CH_2)_{11}OSO_3Na$     F5

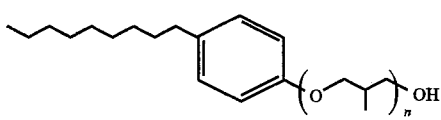

F6 n = ca. 10

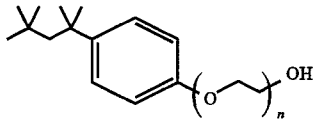

F7 n = ca. 40

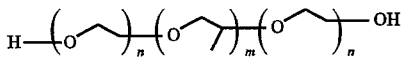

F8 n = ca. 6, m = ca. 22

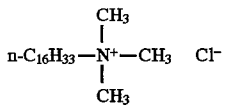

F-9

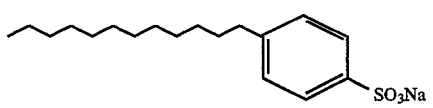

F10

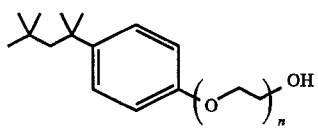

F11 n = ca. 10

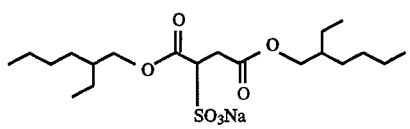

F12

Devices suitable for the high-shear or turbulent mixing of the dispersions of the invention include those generally suitable for preparing submicron photographic emulsified dispersions. These include but are not limited to blade mixers, devices in which a liquid stream is pumped at high pressure through an orifice or interaction chamber, sonication, Gaulin mills, homogenizers, blenders, etc. More than one type of device may be used to prepare the dispersions.

It has been found that many conventional compounds which are used as image light stabilizers for magenta image dyes can severely inhibit the post-process reaction between residual magenta coupler and the epoxy compounds of the invention and thereby suppress the beneficial effects of the epoxy compounds on yellowing. In a preferred embodiment of the invention, the epoxy compounds are used in combination with image stabilizers for the magenta image dye such that there is little or no inhibition of the post-process reaction between the epoxy compound and residual magenta coupler. Such embodiment comprises using an image stabilizer of the following formula STG-A in the photosensitive layer of the elements of the invention comprising a magenta coupler dispersion.

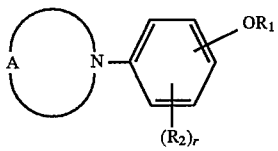
STG-A wherein $R_1$ represents an alkyl group, a cycloalkyl group, an alkenyl phenyl group, an aryl group, a heterocyclic group, an acyl group, a bridged hydrocarbon group, an alkyl sulfonyl group or an aryl sulfonyl group; $R_2$ represents a group capable of being substituted on the benzene ring; r represents an integer between 0 and 4; and A represents a group of non metal atoms necessary for the formation of a 5 to 8 membered ring together with the nitrogen atom. Use of such image stabilizers with residual magenta coupler scavenger epoxy compounds is the subject matter of concurrently filed, commonly assigned, copending application U.S. Ser. No. 08/429,269 (Kodak Docket No. 71731AJA), the disclosure of which is incorporated by reference.

The magenta dye forming coupler in the photographic elements of the invention is preferably a pyrazolone, pyrazolotriazole, pyrazolobenzimidazole with or without a suitable leaving group. The magenta coupler can be monomeric, dimeric, trimeric, oligomeric or polymeric coupler wherein the coupler moiety can be attached to the polymeric backbone via a substituent on the coupler moiety or a substituent on a coupling off group. Illustrative magenta couplers are disclosed in, for example, U.S. Pat. Nos. 1,969,479; 2,311,082; 2,343,703; 2,369,489; 2,575,182; 2,600,788; 2,706,685; 2,908,573; 3,061,432; 3,062,653; 3,152,896; 3,153,816; 3,214,437; 3,253,924; 3,311,476; 3,419,391; 3,519,429; 3,725,067; 3,770,447; 3,907,571; 3,928,044; 3,935,015; 4,120,723; 4,123,281; 4,199,361; 4,336,325; 4,351,897; 4,385,111; 4,401,752; 4,407,936; 4,413,054; 4,283,472; 4,338,393; 4,420,556; 4,443,536; 4,500,630; 4,522,915; 4,540,654; 4,576,912; 4,581,326; 4,621,046; 4,728,598; 4,774,172; and 4,853,319 European Patent Applications Nos. 284,239; 284,240; 240,852; 170, 164; and 177,765; Japanese Patent Publication Nos. 60/170854, 60/194451 and 60/194452 and Great Britain Patents Nos. 1,047,612, 1,357,372 and 1,530,272, and "Farbkuppler-eine Literaturübersicht", published in Agfa Mitteilungen, Band III, pp 126–156 (1961); the disclosures of which are incorporated herein by reference.

Magenta dye-forming couplers comprise pyrazolone compounds of the general formulae:

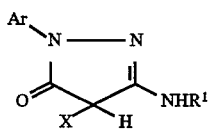
(M-1)

and

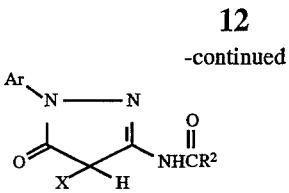
(M-2)

pyrazolotriazole compounds of the general formulae:

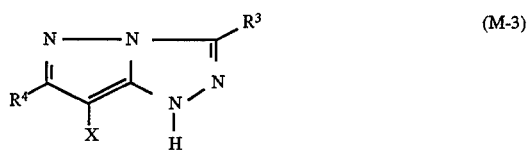
(M-3)

and

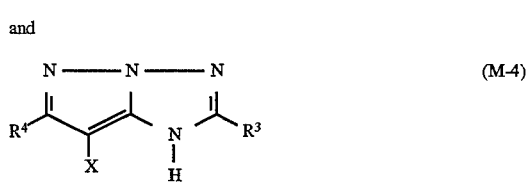
(M-4)

and pyrazolobenzimidazoles of the formula:

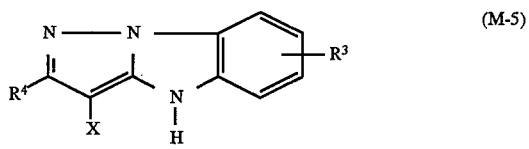
(M-5)

wherein

Ar is an unsubstituted aryl group or an aryl group (including pyridyl) substituted with one or more substituents selected from halogen atoms and cyano, alkylsulfonyl, arylsulfonyl, sulfamoyl, sulfonamido, carbamoyl, carbonamido, alkoxy, acyloxy, aryloxy, atkoxycarbonyl, aryloxycarbonyl, ureido, nitro, alkyl, and trifluoromethyl, or Ar is an aryl group substituted with a group which forms a link to a polymeric chain;

$R^1$ is a substituted or unsubstituted phenyl group and $R^2$ is a substituted or unsubstituted alkyl or phenyl group, the $R^1$ and $R^2$ substituents being individually selected from halogen atoms, and alkyl, aryl, alkoxy, aryloxy, carbonamido, carbamoyl, sulfonamido, sulfamoyl, alkylsulfinyl, arylsulfinyl, alkylsulfonyl, arylsulfonyl, alkoxycarbonyl, aryloxycarbonyl, acyl, acyloxy, ureido, imido, carbamate, heterocyclic, cyano, trifluoromethyl, alkylthio, nitro, carboxyl and hydroxyl groups, provided that $R^1$ and $R^2$ each contain at least 6 carbon atoms or the $R^1$ and $R^2$ substituents may individually comprise a group which forms a link to a polymeric chain;

$R^3$ and $R^4$ are individually selected from the group consisting of hydrogen, substituted and unsubstituted alkyl, substituted and unsubstituted phenyl, substituted and unsubstituted alkoxy, substituted and unsubstituted amino, substituted and unsubstituted anilino, substituted and unsubstituted acylamino, halogens and a group which links to a polymer, provided that the total number of carbon atoms contained in $R^3$ and $R^4$ is at least 6 if neither $R^3$ nor $R^4$ is a group which links to a polymer; and X is hydrogen or a coupling-off group selected from the group consisting of halogens, alkoxy, aryloxy, alkylthio, arylthio, acyloxy, sulfonamido, carbonamido, arylazo, nitrogen-containing heterocyclic and imido groups. Coupling-off groups are well known to those skilled in the photographic art. Generally, such groups determine the equivalency of the coupler and modify the reactivity of the coupler. Coupling-off groups can also advantageously effect the layer in which the coupler is coated or other layers in the photographic material by performing, after release from the coupler, such functions as development inhibition, bleach acceleration, color correction, development acceleration and the like. Representative coupling-off groups include, as noted above, halogens (for example, chloro), alkoxy, aryloxy, alkyl thio, aryl thio, acyloxy, sulfonamido, carbonamido, arylazo, nitrogen-containing heterocyclic groups such as pyrazolyl and imidazolyl, and imido groups such as succinimido and hydantoinyl groups. Except for the halogens, these groups may be substituted if desired. Coupling-off groups are described in further detail in: U.S. Pat. Nos. 2,355,169; 3,227,551; 3,432,521; 3,476,563; 3,617,291; 3,880,661; 4,052,212 and 4,134,766, and in British Patent References Nos. 1,466,728; 1,531,927; 1,533,039; 2,006,755A and 2,017,704A, the disclosures of which are incorporated herein by reference.

Preferred structures of magenta couplers are 4- or 2-equivalent pyrazolone couplers, particularly couplers of the structure:

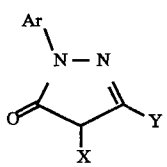

(M-6)

wherein:

Ar is selected from the group consisting of unsubstituted aryl groups, substituted aryl groups and substituted pyridyl groups, the substituents being selected from the group consisting of halogen atoms and cyano, alkylsulfonyl, arylsulfonyl, sulfamoyl, sulfamido, carbamoyl, carbonamido, alkoxy, acyloxy, aryloxy, alkoxycarbonyl, aryloxycarbonyl, ureido, nitro, alkyl and trifluoromethyl groups;

Y is an anilino group substituted with one or more substituents selected from the group consisting of halogen atoms, and alkyl, aryl, alkoxy, aryloxy, carbonamido, carbamoyl, sulfonamido, sulfamoyl, alkylsulfinyl, arylsulfinyl, alkylsulfonyl, arylsulfonyl, alkoxycarbonyl, aryloxycarbonyl, acyl, acyloxy, ureido, imido, carbamate, heterocyclic, cyano, hydroxyl groups, and groups which form a link to a polymeric chain, and wherein Y contains at least 6 carbon atoms; and X is a coupling-off group selected from the group consisting of halogen, alkoxy, aryloxy, alkylthio, arylthio, acyloxy, sulfonamido, sulfonyloxy, carbonamido, arylazo, nitrogen-containing heterocyclic and imido groups.

Coupling-off groups are well known to those skilled in the photographic art. Generally, such groups determine the equivalency of the coupler and modify the reactivity of the coupler. Coupling-off groups can also advantageously effect the layer in which the coupler is coated or other layers in the photographic material by performing, after release from the coupler, such functions as development inhibition, bleach acceleration, color correction, development acceleration and the like. Representative coupling-off groups include, as noted above, halogens (for example, chloro), alkoxy, aryloxy, alkylthio, arylthio, acyloxy, sulfonamido, carbonamido, arylazo, nitrogen-containing heterocyclic groups such as pyrazolyl and imidazolyl, and imido groups such as succinimido and hydantoinyl groups. Coupling-off groups are described in further detail in: U.S. Pat. Nos. 2,355,169; 3,227,551; 3,432,521; 3,476,563; 3,67,291; 3,880,661; 4,052,212 and 4,134,766, and in British Patent Reference Nos. 1,466,788; 1,531,927; 1,533,039; 2,006,755A and 2,017,704A, the disclosures of which are incorporated herein by reference.

Particularly preferred are compounds in which Ar is of the structure:

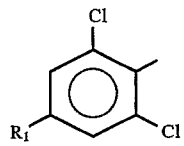

wherein $R_1$ is selected from the group consisting of halogen, cyano, alkylsulfonyl, arylsulfonyl, sulfamoyl, sulfonamido, carbamoyl, carbonamido, ureido, alkoxycarbonyl, aryloxycarbonyl, acyloxy, alkoxy, aryloxy, nitro and trifluoromethyl groups;

Y is of the structure:

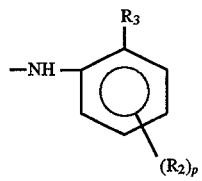

wherein p is from zero to 2 and each $R_2$ is in a meta or para position with respect to $R_3$;

each $R_2$ is individually selected from the group consisting of halogen, alkyl, alkoxy, aryloxy, carbonamido, carbamoyl, sulfonamido, sulfamoyl, alkylsulfinyl, arylsulfinyl, alkylsulfonyl, arylsulfonyl, alkoxycarbonyl, aryloxycarbonyl, acyloxy, ureido, imido, carbamate, heterocyclic, cyano, nitro, acyl, trifluoromethyl, alkylthio and carboxyl groups; and $R_3$ is selected from the group consisting of hydrogen, halogen, alkyl, alkoxy, aryloxy, alkylthio, carbonamido, carbamoyl, sulfonamido, sulfamoyl, alkylsulfonyl, arylsulfonyl, alkoxycarbonyl, acyloxy, acyl, cyano, nitro and trifluoromethyl groups; and X is of the structure:

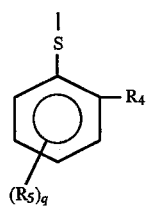

wherein $R_4$ and $R_5$ are individually selected from the group consisting of hydrogen, halogen, alkyl, alkoxy, aryloxy, carbonamido, ureido, carbamate, sulfonamido, carbamoyl, sulfamoyl, acyloxy, alkoxycarbonyl, aryloxycarbonyl, amino and carboxyl groups, and wherein q is 0, 1 or 2 and $R_5$ may be in the meta or para position with respect to the sulfur atom.

Suitable magenta dye-forming couplers for use in the compositions and methods of the present invention include, but are not limited to, the following compounds:

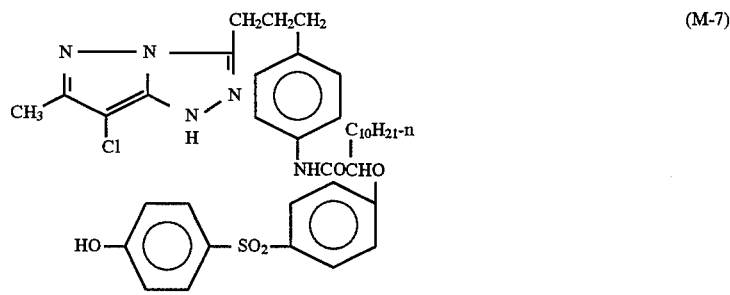
(M-7)
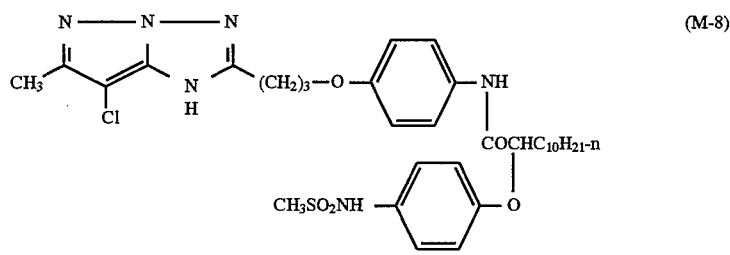
(M-8)
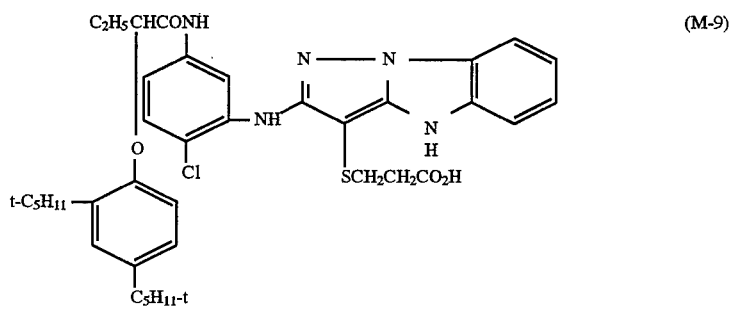
(M-9)
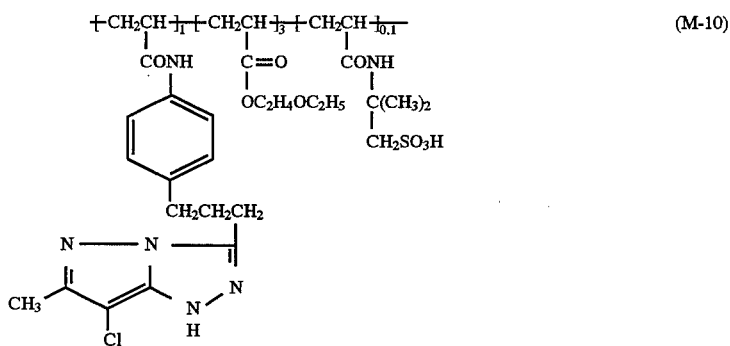
(M-10)
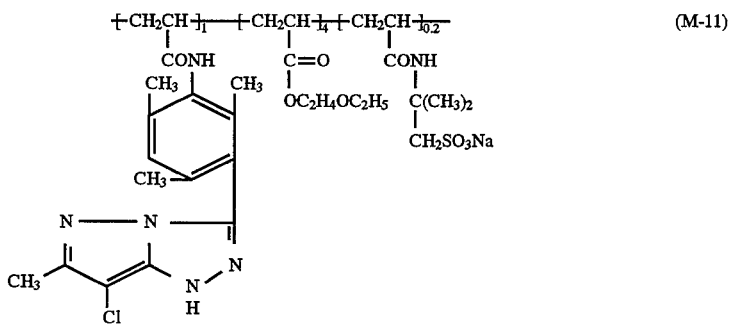
(M-11)

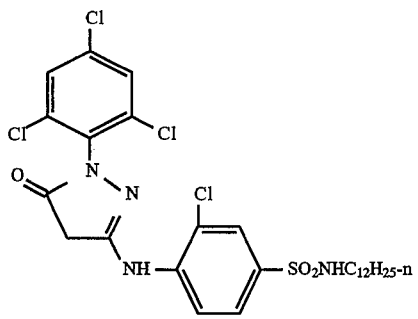
(M-12)
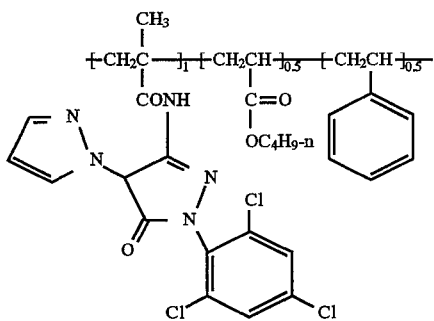
(M-13)
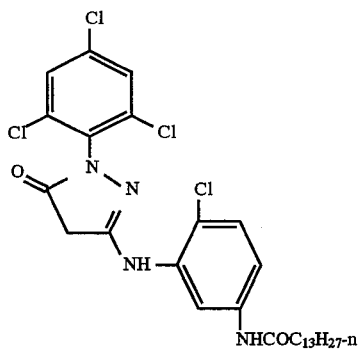
(M-14)
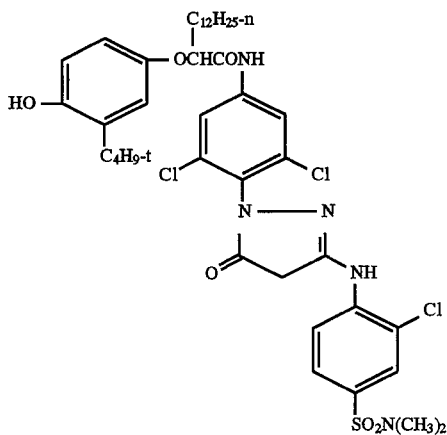
(M-15)

-continued
(M-16)
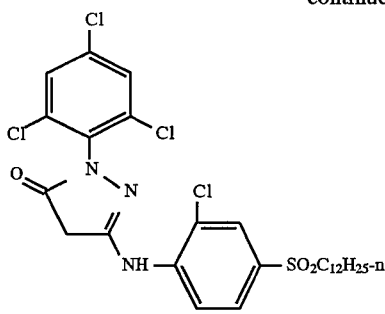
(M-17)
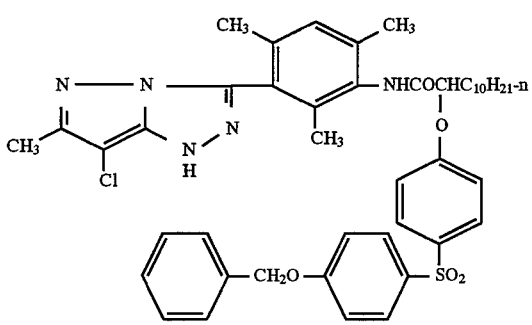
(M-18)
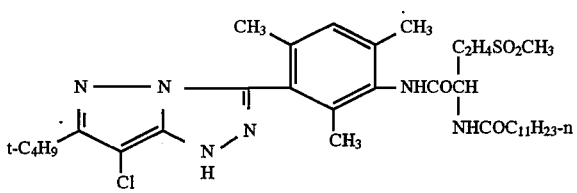
Examples of two-equivalent 3-anilino pyrazolone dye-forming magenta couplers suitable for use in the coupler compositions of the present invention include, but are not limited to the following:
(M-19)
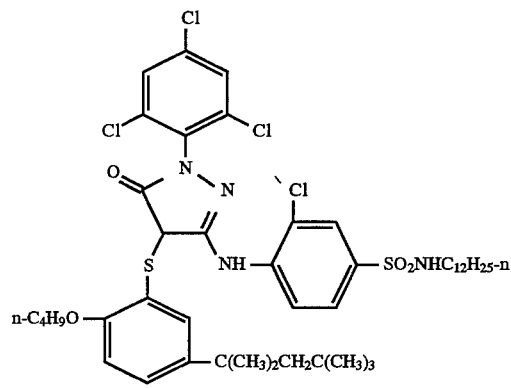

-continued
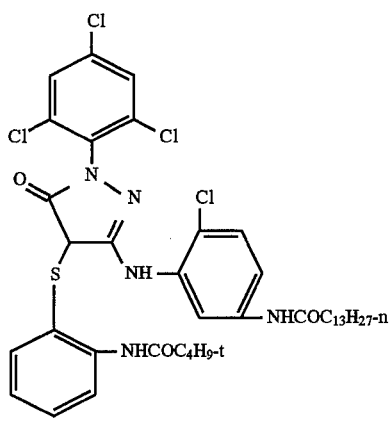
(M-20)
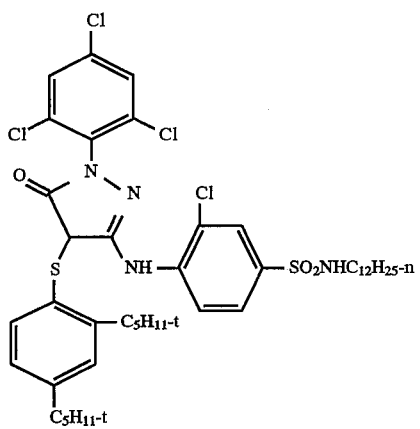
(M-21)
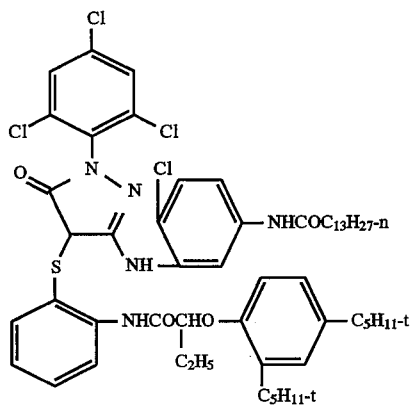
(M-22)
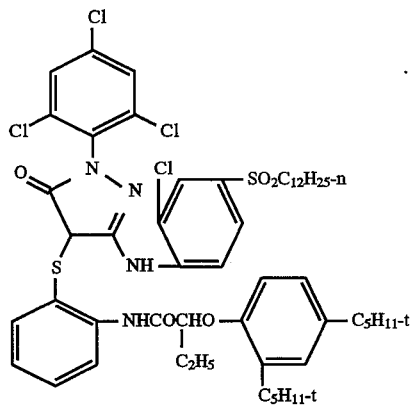
(M-23)

-continued
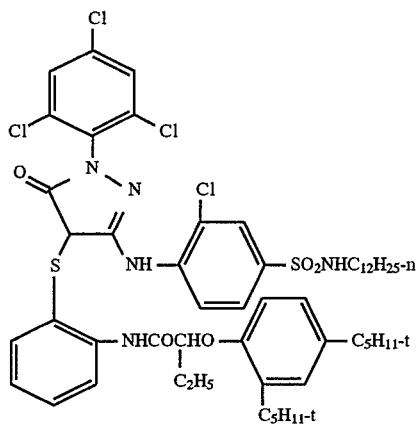
(M-24)
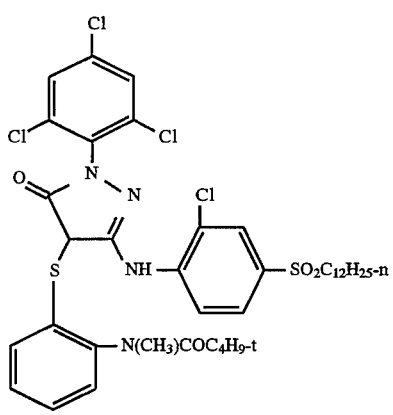
(M-25)
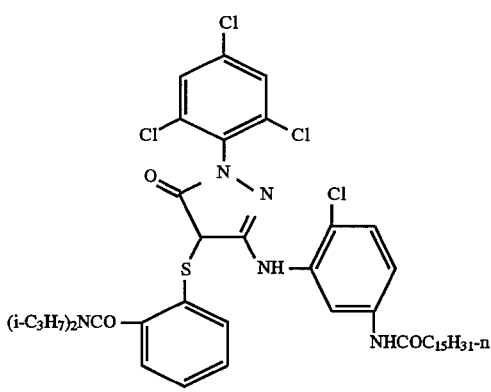
(M-26)
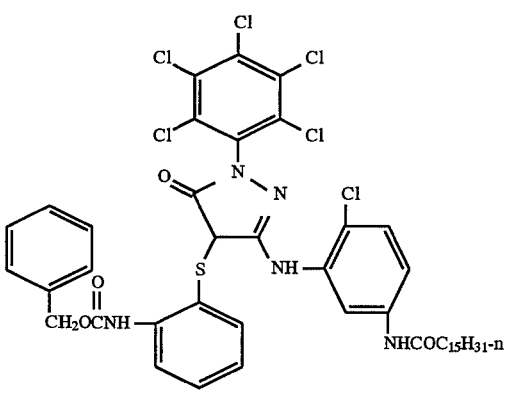
(M-27)

-continued
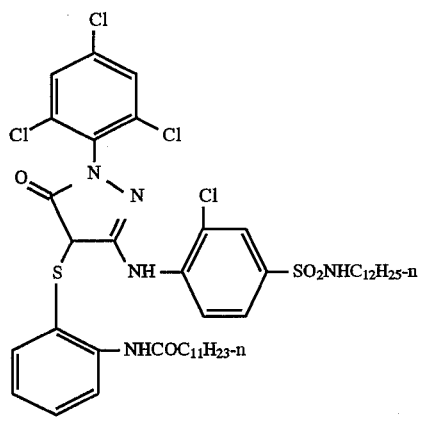
(M-28)
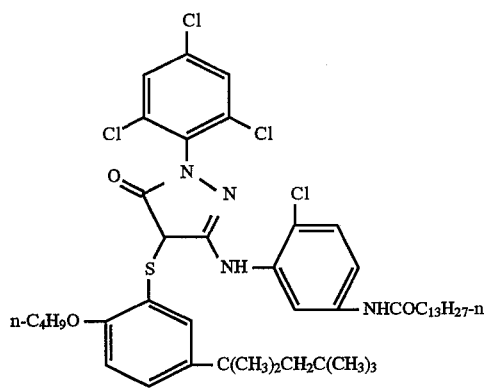
(M-29)
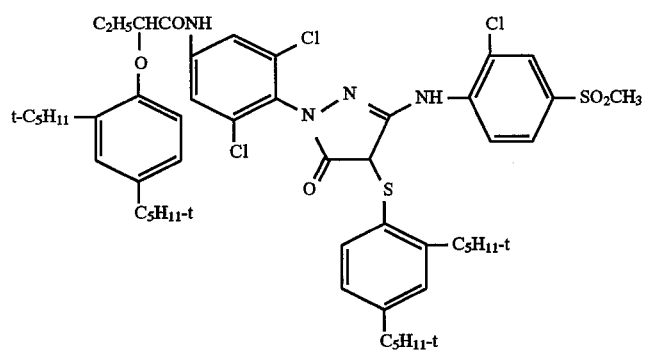
(M-30)
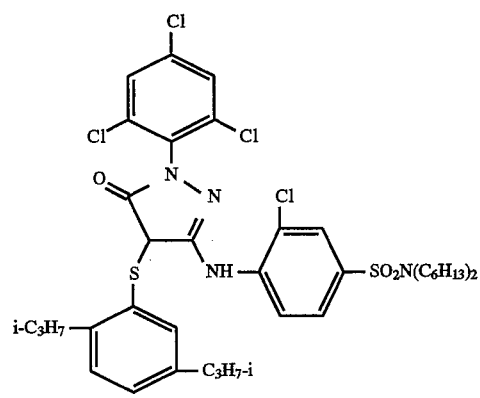
(M-31)

-continued
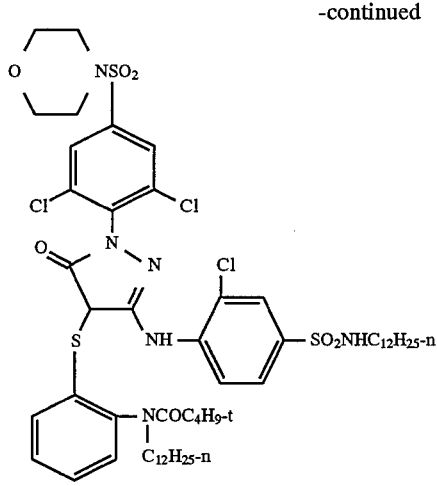
(M-32)
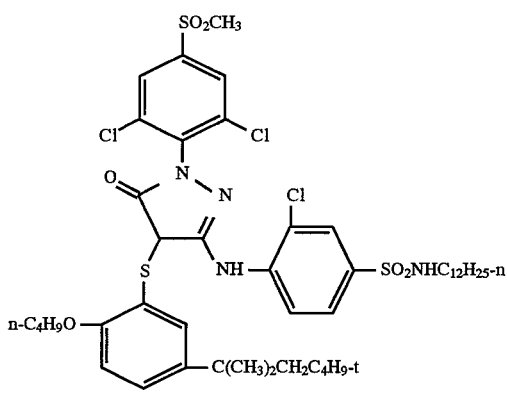
(M-33)
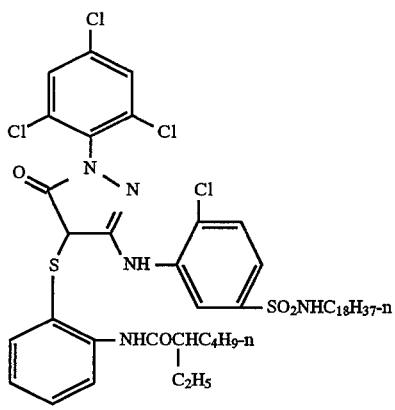
(M-34)
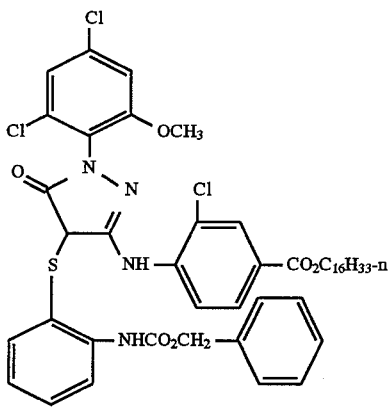
(M-35)

-continued
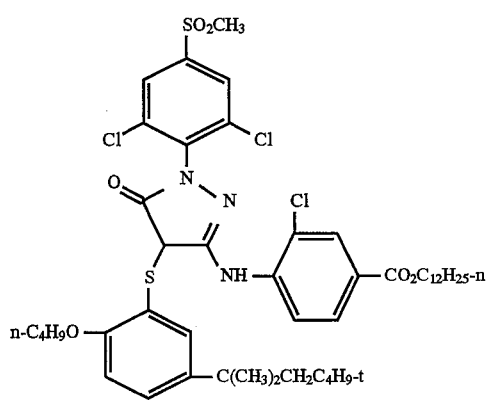
(M-36)
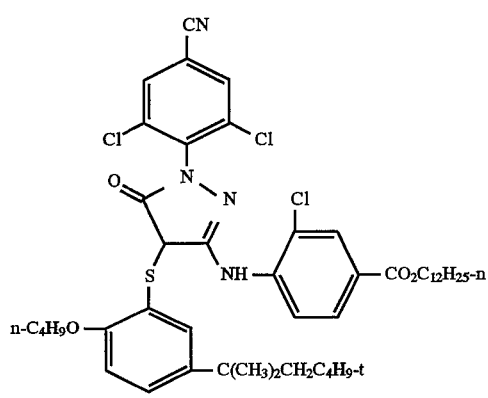
(M-37)
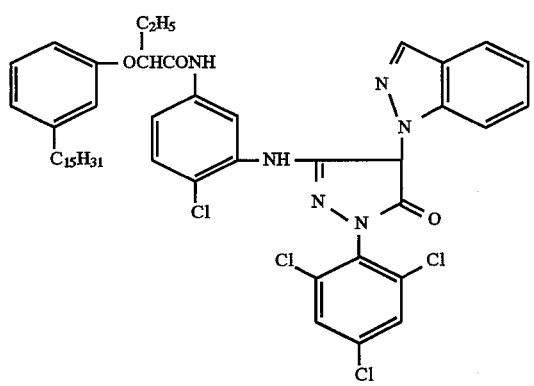
(M-38)
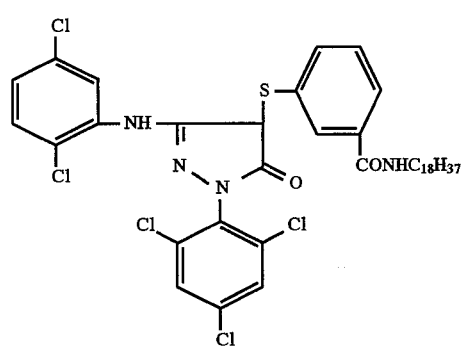
(M-39)

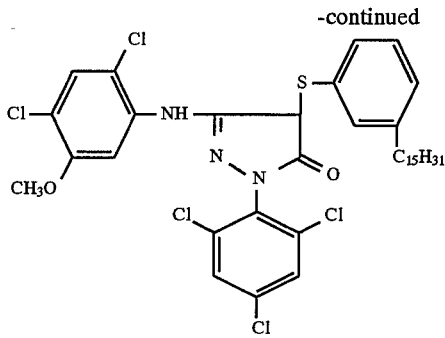

(M-40)

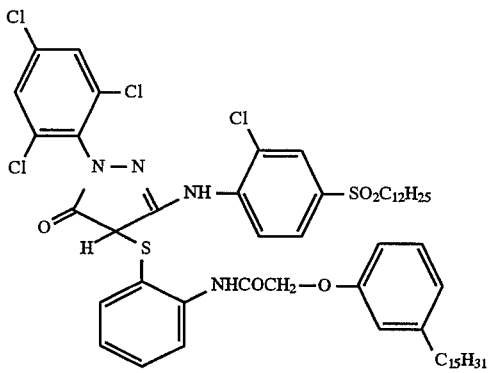

(M-41)

Particularly preferred couplers are compounds of the formulae: M-20, M-21, M-22, M-23, M-24, and M-41.

The color photographic element of this invention comprises, in addition to the magenta coupler-containing layer and the layer comprising the epoxy compound, various other layers typically included in color photographic elements.

Multicolor color photographic elements typically contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

Use of compounds of formula SI in multilayer photographic elements is specifically contemplated. A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like. For example, compounds of formula SI may be used in layers adjacent to the magenta layers of the multilayer elements described in Research Disclosure February 1995, Item 37038, published by Kenneth Mason Publications, Ltd., Dudley Annex, 12a North Street, Emsworth, Hampshire P010 7DQ, ENGLAND, the disclosure of which is hereby incorporated by reference.

If desired, the photographic element can be used in conjunction with an applied magnetic layer as described in Research Disclosure, November 1992, Item 34390, incorporated herein by reference.

In the following discussion of suitable materials for use in the photographic element of this invention, reference will be made to Research Disclosure, December 1989, Item 308119, available as described above, which will be identified hereafter by the term "Research Disclosure." The contents of the Research Disclosure, including the patents and publications referenced therein, are incorporated herein by reference, and the Sections hereafter referred to are Sections of the Research Disclosure.

The silver halide emulsions employed in the elements of this invention can be either negative-working or positive-working. Suitable emulsions and their preparation as well as methods of chemical and spectral sensitization are described in Sections I through IV. Color materials and development modifiers are described in Sections V and XXI. Vehicles are described in Section IX, and various additives such as brighteners, antifoggants, stabilizers, light absorbing and scattering materials, hardeners, coating aids, plasticizers, lubricants and matting agents are described, for example, in Sections V, VI, VIII, X, XI, XII, and XVI. Manufacturing methods are described in Sections XIV and XV, other layers and supports in Sections XIII and XVII, processing methods and agents in Sections XIX and XX, and exposure alternatives in Section XVIII.

The photographic element of this invention generally contains image dye-forming couplers that form cyan dyes upon reaction with oxidized color developing agents which are described in such representative patents and publications as: U.S. Pat. Nos. 2,772,162, 2,895,826, 3,002,836, 3,034,892, 2,474,293, 2,423,730, 2,367,531, 3,041,236, 4,883,746 and "Farbkuppler-eine Literature Ubersicht," published in Agfa Mitteilungen, Band III, pp. 156–175 (1961). Preferably such couplers are phenols and naphthols that form cyan dyes on reaction with oxidized color developing agent.

As discussed above, the photographic element of this invention contains an image dye-forming coupler that forms a magenta dye. Illustrative magenta couplers are set forth above.

The photographic element can also contain couplers that form yellow dyes upon reaction with oxidized and color developing agent are described in such representative patents and publications as: U.S. Pat. Nos. 2,875,057, 2,407, 210, 3,265,506, 2,298,443, 3,048,194, 3,447,928 and "Farbkuppler-eine LiteratureUbersicht," published in Agfa Mitteilungen, Band III, pp. 112–126 (1961). Such couplers are typically open chain ketomethylene compounds.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may also be used in association with "wrong" colored couplers (e.g. to adjust levels of interlayer correction) and, in color negative applications, with masking couplers such as those described in EP 213,490; Japanese Published Application 58-172,647; U.S. Pat. No. 2,983,608; German Application DE 2,706,117C; U.K. Patent 1,530,272; Japanese Application A-113935; U.S. Pat. Nos. 4,070,191 and 4,273,861; and German Application DE 2,643,965. The masking couplers may be shifted or blocked.

The photographic element can also contain materials that accelerate or otherwise modify the processing steps e.g. of bleaching or fixing to improve the quality of the image. Bleach accelerator releasing couplers such as those described in EP 193,389; EP 301,477; U.S. Pat. No. 4,163, 669; U.S. Pat. No. 4,865,956; and U.S. Pat. No. 4,923,784, may be useful. Also contemplated is use of nucleating agents, development accelerators or their precursors (UK Patent 2,097,140; U.K. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

In a color paper format, the photographic element of the invention may comprise a support bearing the following layers from top to bottom:

(1) one or more overcoats;

(2) a cyan layer containing "Coupler 1". Butanamide, 2-(2,4-bis(1,1-dimethylpropyl)phenoxy)-N-(3,5-dichloro-2-hydroxy-4-methylphenyl)-, "Coupler 2": Acetamide, 2-(2,4-bis(1,1-dimethylpropyl)phenoxy)-N-(3,5-dichloro-2-hydroxy-4-, and UV Stabilizers: Phenol, 2-(5-chloro-2H-benzotriazol-2-yl)-4,6-bis(1,1-dimethylethyl)-;Phenol, 2-(2H-benzotriazol-2-yl)-4-(1,1-dimethylethyl)-;Phenol, 2-(2H-benzotriazol-2-yl)-4-(1,1-dimethylethyl)-6-(1-methylpropyl)-; and Phenol, 2-(2H-benzotriazol-2-yl)-4,6-bis(1,1-dimethylpropyl)- and a poly(t-butylacrylamide) dye stabilizer;

(3) an interlayer;

(4) a magenta layer containing "Coupler 3": Octanamide, 2-[2,4-bis(1,1-dimethylpropyl)phenoxy]-N-[2-(7-chloro-6-methyl-1H-pyrazolo[1,5-b][1,2,4]-triazol-2-yl)propyl]-together with 1,1'-Spirobi(1H-indene), 2,2',3,3'-tetrahydro-3,3,3',3'-tetramethyl-5,5',6,6'-tetrapropoxy-;

(5) an interlayer; and (6) a yellow layer containing "Coupler 4": 1Imidazolidineacetamide, N-(5-((2-(2,4-bis(1,1-dimethylpropyl)phenoxy)-1-oxobutyl)amino)-2-chlorophenyl)-.alpha.-(2,2-dimethyl-1-oxopropyl)-4-ethoxy-2,5-dioxo-3-(phenylmethyl)-.

The photographic element of the invention can also contain filter dye layers comprising colloidal silver sol or yellow, cyan, and/or magenta filter dyes, either as oil-in-water dispersions, latex dispersions or as solid particle dispersions. Additionally, the photographic element can contain "smearing" couplers (e.g. as described in U.S. Pat. No. 4,366,237; EP 96,570; U.S. Pat. No. 4,420,556; and U.S. Pat. No. 4,543,323.)

The photographic element can also contain image-modifying compounds such as "Developer Inhibitor-Releasing" compounds (DIR's). DIR's useful in conjunction with the compositions of the invention are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

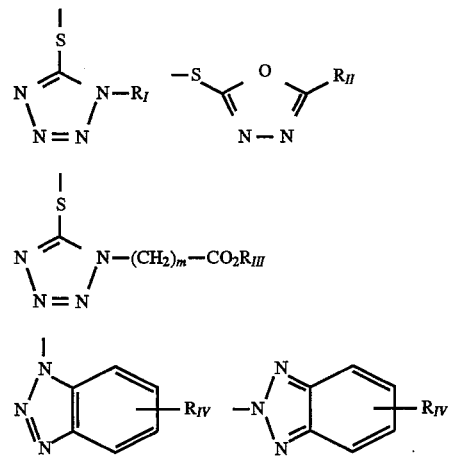

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

As mentioned, the developer inhibitor-releasing coupler may include a timing group which produces the time-delayed release of the inhibitor group such as groups utilizing the cleavage reaction of a hemiacetal (U.S. Pat. No. 4,146,396, Japanese Applications 60-249148; 60-249149); groups using an intramolecular nucleophilic substitution reaction (U.S. Pat. No. 4,248,962); groups utilizing an electron transfer reaction along a conjugated system (U.S. Pat. No. 4,409,323; 4,421,845; Japanese Applications 57-188035; 58-98728; 58-209736; 58-209738) groups utilizing ester hydrolysis (German Patent Application (OLS) No. 2,626,315; groups utilizing the cleavage of imino ketals (U.S. Pat. No. 4,546,073); groups that function as a coupler or reducing agent after the coupler reaction (U.S. Pat. No. 4,438,193; U.S. Pat. No. 4,618,571) and groups that combine the features describe above. It is typical that the timing group or moiety is of one of the formulas:

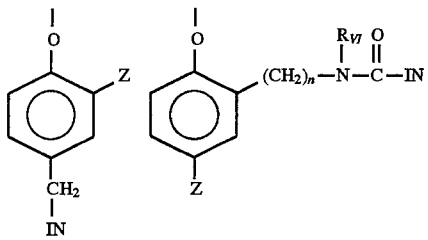

wherein IN is the inhibitor moiety, Z is selected from the group consisting of nitro, cyano, alkylsulfonyl; sulfamoyl (—$SO_2NR_2$); and sulfonamido (—$NRSO_2R$) groups; n is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

Suitable developer inhibitor-releasing couplers for use in the present invention include, but are not limited to, the following:

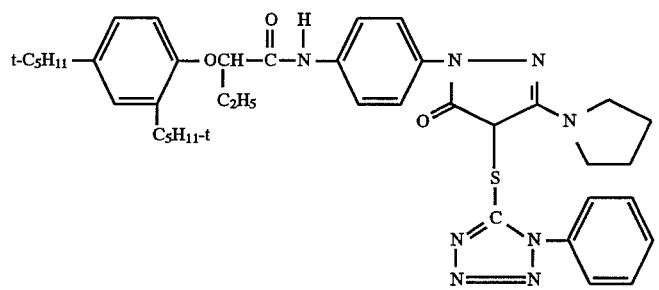

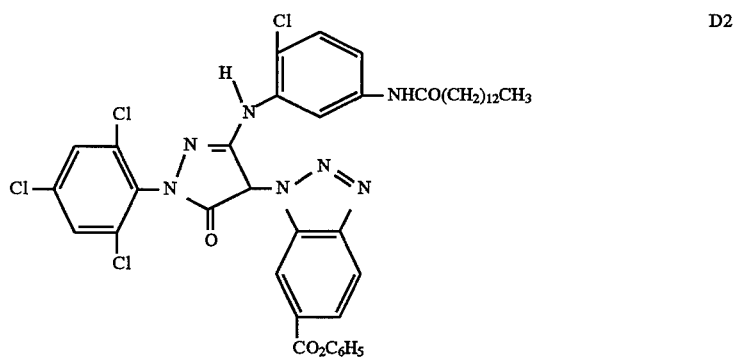

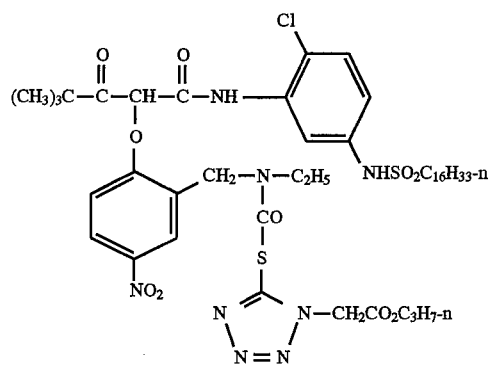
D3
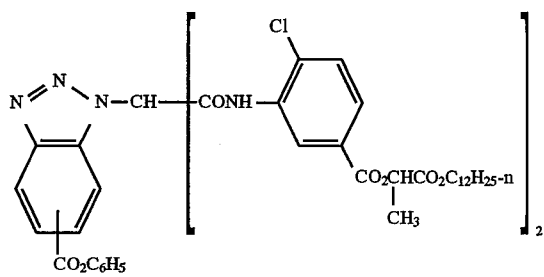
D4
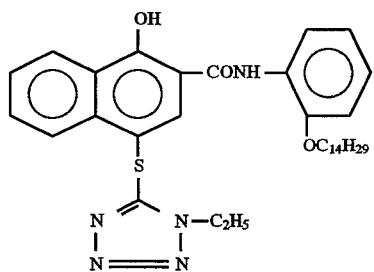
D5
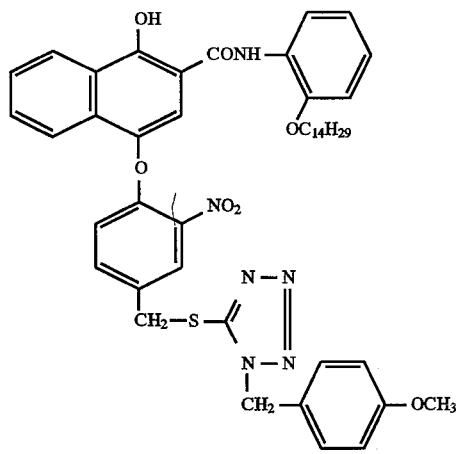
D6

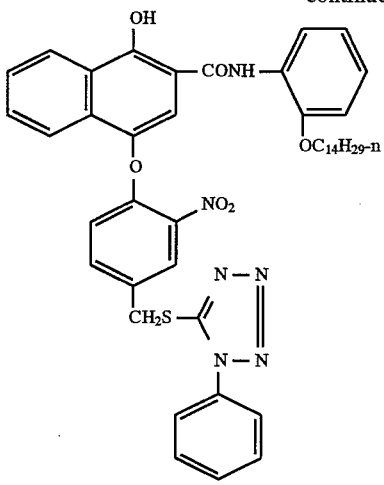

D7

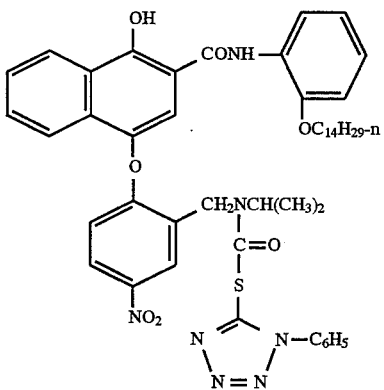

D8

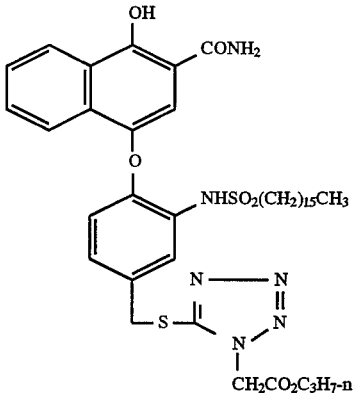

D9

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. Other compounds that can be included in the photographic element of this invention are disclosed in Japanese Published IO Applications described in Derwent Abstracts having accession numbers as follows: 90-072,629, 90-072,630; 90-072,631; 90-072,632; 90-072,633; 90-072,634; 90-077, 822; 90-078,229; 90-078,230; 90-079,336; 90-079,337; 90-079,338; 90-079,690; 90-079,691; 90-080,487; 90-080, 488; 90-080,489; 90-080,490; 90-080,491; 90-080,492; 90-080,494; 90-085,928; 90-086,669; 90-086,670; 90-087, 360; 90-087,361; 90-087,362; 90-087,363; 90-087,364; 90-088,097; 90-093,662; 90-093,663; 90-093,664; 90-093, 665; 90-093,666; 90-093,668; 90-094,055; 90-094,056; 90-103,409; 83-62,586; 83-09,959.

Especially useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T = ECD/t^2$$

where

ECD is the average equivalent circular diameter of the tabular grains in microns and t is the average thickness in microns of the tabular grains.

The average useful ECD of photographic emulsions can range up to about 10 microns, although in practice emulsion ECD's seldom exceed about 4 microns. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micron) tabular grains. To achieve the lowest levels of granularity it is preferred that aim tabular grain projected areas be satisfied with ultrathin (t<0.06 micron) tabular grains. Tabular grain thicknesses typically range down to about 0.02 micron. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micron.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616. In addition, use of [100] silver chloride emulsions as described in EP 534,395 are specifically contemplated.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

The photographic elements can be processed, for example, in accordance with color print processes such a the RA-4 process of Eastman Kodak Company as described in the British Journal of Photography Annual of 1988, Pp 198–199.

Preferred color developing agents are p-phenylenediamines such as:

4-amino-N,N-diethylaniline hydrochloride, 4-amino-3-methyl-N,N-diethylaniline hydrochloride, 4-amino-3-methyl-N-ethyl-N-(b-(methanesulfonamido) ethyl)aniline sesquisulfate hydrate, 4-amino-3-methyl-N-ethyl-N-(b-hydroxyethyl)aniline sulfate, 4-amino-3-b-(methanesulfonamido)ethyl-N,N-diethylaniline hydrochloride and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

SYNTHESIS EXAMPLE

The following synthesis example is representative of synthetic procedures which may be used to prepare epoxy compounds of the invention.

Synthesis of SI-4: Reaction of p-Aminophenol with Benzene Sulfonyl Chloride. Synthesis of 1A.

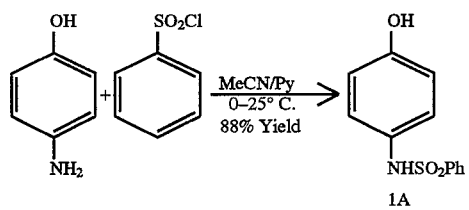

A 2 L 3 n-flask equipped with a mechanical stirrer, thermometer and a pressure equalized addition funnel was charged with p-aminophenol (154.47 g, 1.416 mol), and MeCN (1L). This solution was chilled in a ice/water bath for 10 min while stirring under an Argon atmosphere. To this cold (internal temperature: 10° C.) tan solution pyridine (116.5 mL, 1.444 mol) was added in two portions and the let stir for 20 min. A pressure equalized addition funnel was charged with benzene sulfonyl chloride (250 g, 1.416 mol), and was then added dropwise over 1 h at which time the reaction was removed from the cold bath and allowed to warm to room temperature. A color change from pink/orange to red was observed during addition. The reaction was stirred for 1 h, internal temperature: 15°–20° C., reaction was complete by tlc analysis. Reaction mixture was poured into ice water (1900 mL) with conc. HCl (100 mL) and partitioned with EtOAc (7500 mL), and transferred to separatory funnel. Layers were separated and aqueous layer was extracted with EtOAc (2×750 mL), organic layers were combined, washed with 1N HCl (1×500 mL), brine (1×500 mL), dried over MgSO$_4$, treated with Darco® filtered and stripped to give an off white solid (354 g). Crude product was digested in a minimum of EtOAc, chilled and collected a snow white crystalline solid, washed with Ligroin 950 and dried in a vac oven for 18 hr at 80° C. to give 1A, 270.59 g (77%) of a white crystalline solid. Filtrate was concentrated and diluted with Ligroin 950 to give two additional crops (41.49 g) of pure product, giving a total yield of 312.08 g, mp 156°–157 ° C., (88%). $^1$H NMR (300 MHz) DMSO: δ6.55 (d, J=8.7 Hz, 2H), 6.78 (d, J=8.7 Hz, 2H), 7.44–7.53 (m, 3H), 7.61 (d, J=7.1 Hz, 2H), 9.29 (s, 1H), 9.70 (s, 1H).

Reaction of Benzene Sulfonamido-Phenol with Undecenoyl Chloride. Synthesis of 1B.

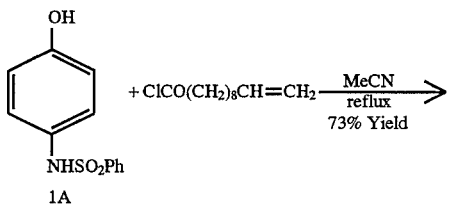

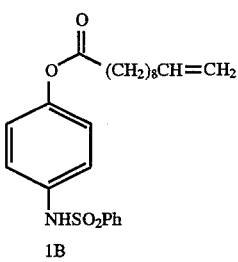

A 1L flask equipped with a magnetic stirring bar was charged with 1A (87.67 g, 351.68 mmol), MeCN (300 mL), and undecenoyl chloride (71.30 g, 351.68 mmol). The mixture was then warmed to reflux of 1 h. Reaction was monitored by tlc til complete (72 h); required additional undecenoyl chloride (4.0 g, 19.73 mmol, 0.06 Eq.) to consume all of starting phenol. Tlc analysis shows a major polar spot for product and a trace of less polar bis-acylated material. Reaction mixture was stripped to give an amber oil, which was re-dissolved in EtOAc (750 mL). Transferred to a separatory funnel and washed with water (1×250 mL), brine (1×250 mL), dried over MgSO$_4$, filtered and stripped to give an amber oil (148.7 g). $^1$H NMR of crude product shows product purity aprox. 95%. Crude product was chromatographed over silica gel (400–600μ) and eluted with 8:1 and 4:1 ligroin 950/EtOAc. Fractions were pooled and solvent stripped to give: the desired product (1B), as a pale yellow oil (105.70 g, 73%). FDMS Large m/e=415. $^1$H NMR (300 MHz) CDCl$_3$: δ1.31 (m, 10H), 1.68 (m, 2H), 2.03 (m, 2H), 2.50 (t, J=7.5 Hz, 2 H), 4.94 (m, 2H), 5.79 (m, 1H), 6.92 (d, J=8.8 Hz, 2 H), 7.05 (m, 3H), 7.40 (d, J=7.2 Hz, 2H), 7.52 (d, J=7.3 Hz, 1H), 7.74 (d, J=7.2 Hz, 2H).

Reaction of Benzene Sulfonamido-Phenyl Undecenoate with m-Chloro-perbenzoic acid. Synthesis of SI-4.

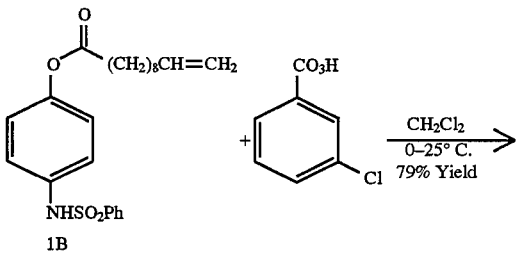

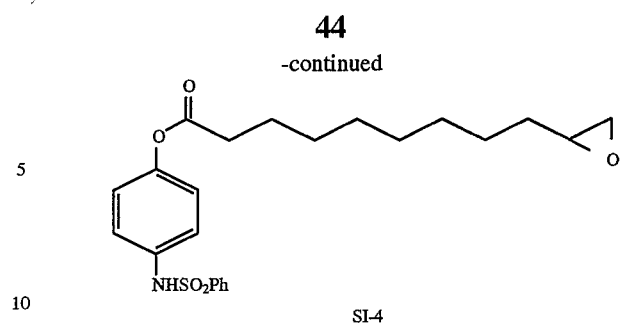

A 1L flask equipped with a magnetic stirring bar and a pressure equalized addition funnel was charged with 1B (67.93 g, 163.47 mmol), CH$_2$Cl$_2$ (250 mL). This solution was chilled in an ice water bath for 30 min. A pressure equalized addition funnel was charged with a solution of m-perbenzoic acid (80%, tech. grade; 46.0 g, 212.5 mmol) in CH$_2$Cl$_2$ (400 mL)†. The m-CPBA solution was then added dropwise over 3 h and the reaction let stir for 24 hrs at room temperature, during this time a white precipitate had formed (CBA). Tlc analysis (4:1 ligroin 950/EtOAc) showed complete conversion of starting material. White solids were filtered off and discarded; tlc analysis matched authentic sample of CBA. Filtrate was transferred to a separatory funnel and treated with a solution of 10% Na$_2$SO$_3$ (250 ml), separated layers, aqueous layer was discarded, and organic layer was washed with 10% NaHCO$_3$ (1×250 mL), brine (1×250 mL), and dried (MgSO$_4$), filtered and stripped to give a yellow oil (66.2 g, 94%). Crude product was chromatographed over silica gel (400–600μ) and eluted with 4:1 ligroin 950/EtOAc. Fractions were pooled and solvent stripped to give SI-4 as a pale amber oil 55.77 g (79%). FDMS Large m/e=431. $^1$H NMR (300 MHz) CDCl$_3$: δ1.24–1.52 (m, 10H), 1.68 (m, 2H), 2.48 (m, 3H), 2.74 (m, 1H), 2.90 (m, 1H), 6.91 (d, J=8.7 Hz, 2H), 7.03 (d, J=8.7 Hz, 2H), 7.42 (m, 3H), 7.51 (d, J=7.3 Hz, 1H), 7.73 (d, J=8.3 Hz, 2H). Tg=−35° C., melting point <−160° C.

The following examples illustrate the invention.

EXAMPLE 1

A dispersion of the control compound, a solid terminal epoxide, E1 (logP=4.5, melting point 77° C.) was prepared in the following manner.

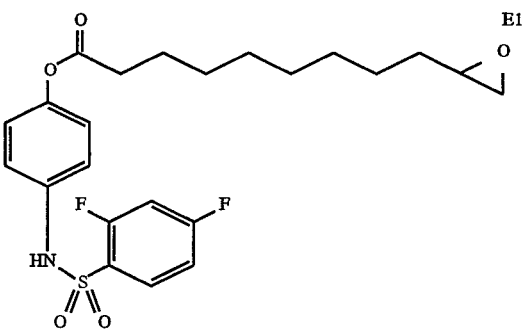

3.0 grams of E1 was combined with 1.0 gram of the water-immiscible organic solvent tri(2-ethylhexyl) phosphate. The mixture was heated until the oil phase was homogeneous. 26.0 grams of a 12% w/w solution of Type IV gelatin in water was combined with 43.8 grams of water and 4.0 grams of Alkanol XC to constitute the aqueous phase. The aqueous phase was maintained at 70° C. The oil phase was combined with the aqueous phase while stirring. The mixture was then passed twice through the microfluidizer at a pressure of 10,000 psi to obtain the dispersion.

A dispersion of the liquid terminal epoxide compound SI-4 (logP=4.3, melting point less than −160° C. and a liquid at room temperature, (25° C.)) was prepared in the same manner as above.

Both dispersions were placed in a constant temperature bath set at 45° C. It was found that the dispersion of the control compound E1 disintegrated (with significant settling) after just 6 hours. However, the dispersion of the invention compound SI-4 showed no evidence of settling or macroscopic coagulation even after 12 hours.

EXAMPLE 2

A dispersion of the magenta coupler M-24 was prepared in the following manner. 14.73 grams of the coupler solvent tri(2-ethylhexyl) phosphate was heated to a temperature of 120° C. and combined with 8.50 grams of image stabilizer STG-A1, 2.83 grams of ST-2 and 3.4 grams of ST-3. This was then combined with 12.75 grams of M-24 to constitute the oil phase. The aqueous phase was prepared by mixing 88.5 grams of a 24% w/w solution of Type IV gelatin with 21.2 grams of a 10% w/w solution of the surfactant Alkanol XC and 273 grams of distilled water. The latter was then heated to 70° C. The oil phase was then combined with the aqueous phase and the mixture passed twice through a microfluidizer at a pressure of 10,000 psi at 70° C. to obtain the dispersion.

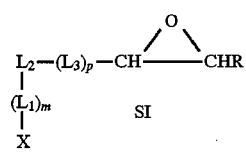
STG-A1

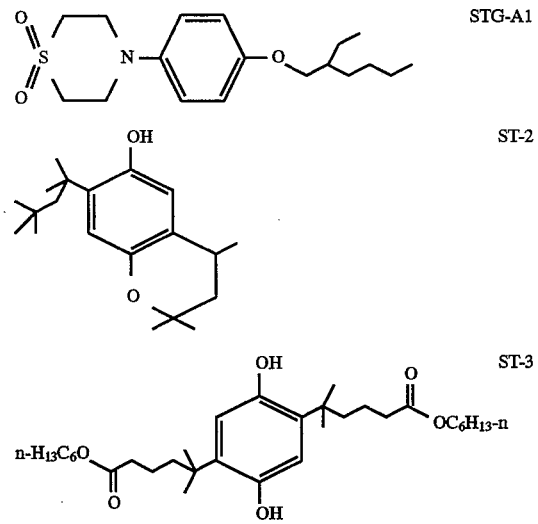

ST-2

ST-3

A dispersion of the epoxide compound SI-4 was made in the same manner as described in Example 1 except that 2.0 grams of tri(2-ethylhexyl) phosphate was used instead of 1.0 gram.

The dispersion of M-24 and the dispersion of SI-4 were then coated on a paper support using the layer format shown below.

| 215 SI-4 | 630 Gel | |
|---|---|---|
| 172 AG | 430 M-24 | 1270 Gel |
| 215 SI-4 | 753 Gel | |

All numbers refer to coverages in mg/m². The coatings also contain a UV protection layer and an overcoat (not shown). A second set of coatings containing no SI-4 were prepared to serve as a control. 35 mm strips from these coatings were exposed using a 21 step tablet and processed using the standard RA-4 process. The processed strips were then stored at room temperature for six weeks and then subjected to 2 weeks of 50 Klux high intensity daylight radiation. The change in blue reflection density in the Dmin (unexposed) region was noted. The results are as follows:

| | D Blue Dmin |
|---|---|
| Control | 0.22 |
| Invention | 0.10 |

It is clear that the method of the invention results in significant improvement in photochemical yellowing.

What is claimed is:

1. A method of preparing a photographic element comprising
  a) forming an aqueous dispersion of an epoxy compound of the structural formula SI:

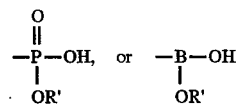

wherein:
  R is H, an alkyl group, or an aryl group;
  $L_1$ is an alkyl group or an aryl group;
  $L_2$ is —O—, —CO—, —S—, —SO$_2$—, —PO$_2$—, —CO$_2$—, —NHCO— or —NHSO$_2$—, wherein $L_2$ may be orientated in either direction;
  $L_3$ is an alkyl group;
  m is 0 or 1;
  p is 0 or 1;
  X is
  —NHSO$_2$R', —SO$_2$NHR', $$-\overset{\overset{\displaystyle O}{\|}}{\underset{\underset{\displaystyle OR'}{|}}{P}}-OH, \text{ or } -\overset{}{\underset{\underset{\displaystyle OR'}{|}}{B}}-OH$$

wherein R' is H or an alkyl or aryl group, with the proviso that where $L_2$ comprises an ionizable group, X may also be an alkyl group or an aryl group; wherein the compound has a melting point of less than about 50° C. and the dispersion is formed by adding the compound in a liquid state to an aqueous solution, and directly dispersing the compound in the aqueous solution;
  (b) coating on a support a photosensitive first layer comprising
    (i) a silver halide emulsion and
    (ii) a magenta coupler dispersed therein; and
  (c) coating on the support a second layer comprising an epoxy compound dispersion prepared according to step (a).

2. A method according to claim 1, wherein the compound is dispersed in the aqueous solution along with an organic solvent.

3. A method according to claim 2, wherein the organic solvent is a high boiling permanent solvent.

4. A method according to claim 1, wherein the compound has a melting point below 25° C.

5. A method according to claim 1, wherein the compound is of the formula

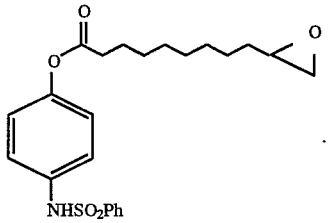

6. A method of preparing a photographic element according to claim 1, wherein m and p are each 1; $L_1$ is phenyl; $L_2$ is —O—, —CO—, —SO$_2$—, —PO$_2$—, or —CO$_2$—; $L_3$ is a linear or branched alkyl group; X is —NHSO$_2$R', —SO$_2$NHR',

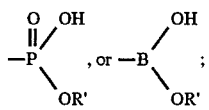

and R' is a phenyl group.

7. A method of preparing a photographic element according to claim 6, wherein the compound is of the formula:

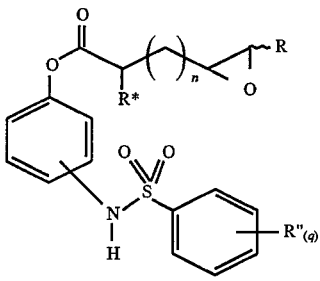

wherein:
- R* is H or an alkyl or aryl group;
- n is from 1 to about 20;
- q is 1, 2, or 3; and
- each R" is H, an alkoxide group, a phosphate group, a sulfate group, a sulfonamide group, a sulfone group, a halogen atom, or an alkyl group; with the proviso the appended sulfonamido group is in a meta or para position with respect to the —CO$_2$— linking group, and with the further proviso when the appended sulfonamido group is in the para position each R" is H, or at least one appended R" group which is not H is in the meta or ortho position with respect to the —NHSO$_2$— linking group, or R* is not H.

8. A method according to claim 7, wherein the appended sulfonamido group is in a meta position with respect to the —CO$_2$— linking group.

* * * * *